(12) United States Patent
Wanasek

(10) Patent No.: US 8,452,399 B2
(45) Date of Patent: May 28, 2013

(54) CONSTANT CURRENT PACING APPARATUS WITH PROTECTION FROM HIGH VOLTAGE PULSES

(75) Inventor: Kevin A. Wanasek, Princeton, MN (US)

(73) Assignee: Medtronic, Inc., Minneapolis, MN (US)

( * ) Notice: Subject to any disclaimer, the term of this patent is extended or adjusted under 35 U.S.C. 154(b) by 652 days.

(21) Appl. No.: 12/604,082

(22) Filed: Oct. 22, 2009

(65) Prior Publication Data

US 2010/0324619 A1 Dec. 23, 2010

Related U.S. Application Data

(60) Provisional application No. 61/219,652, filed on Jun. 23, 2009, provisional application No. 61/219,642, filed on Jun. 23, 2009.

(51) Int. Cl.
*A61N 1/36* (2006.01)

(52) U.S. Cl.
USPC .......................................................... 607/9

(58) Field of Classification Search
USPC .......................................................... 607/9
See application file for complete search history.

(56) References Cited

U.S. PATENT DOCUMENTS

| | | | |
|---|---|---|---|
| 4,216,780 A | 8/1980 | Rubel et al. | |
| 5,018,522 A | 5/1991 | Mehra | |
| 5,117,824 A | 6/1992 | Keimel et al. | |
| 5,333,617 A | 8/1994 | Hafner | |
| 5,540,729 A | 7/1996 | Weijand | |
| 5,591,218 A | 1/1997 | Jacobson | |
| 5,782,880 A | 7/1998 | Lahtinen et al. | |
| 5,836,983 A | 11/1998 | Weijand et al. | |
| 5,861,013 A | 1/1999 | Peck et al. | |
| 5,939,931 A | 8/1999 | Noro | |
| 5,941,906 A | 8/1999 | Barreras, Sr. et al. | |
| 6,035,235 A | 3/2000 | Perttu et al. | |
| 6,209,764 B1 | 4/2001 | Hartlaub et al. | |
| 6,952,608 B2 | 10/2005 | Ostroff | |
| 6,963,773 B2 | 11/2005 | Waltman et al. | |
| 6,968,230 B2 * | 11/2005 | Waltman | 607/4 |
| 7,010,350 B2 | 3/2006 | Kralik | |
| 7,136,702 B2 | 11/2006 | Wanasek | |
| 7,194,303 B2 | 3/2007 | Rissmann et al. | |
| 7,200,434 B2 | 4/2007 | Havel et al. | |
| 7,236,018 B1 | 6/2007 | Wang et al. | |
| 7,877,139 B2 * | 1/2011 | Ostroff | 607/8 |
| 8,155,740 B2 | 4/2012 | Wanasek | |
| 2005/0288714 A1 | 12/2005 | Ostroff | |
| 2007/0179537 A1 | 8/2007 | Rissmann et al. | |
| 2010/0249867 A1 | 9/2010 | Wanasek | |
| 2010/0324618 A1 | 12/2010 | Wanasek | |

FOREIGN PATENT DOCUMENTS

| | | |
|---|---|---|
| WO | WO2005/115538 A1 | 12/2005 |
| WO | WO2010/114655 A1 | 10/2010 |

OTHER PUBLICATIONS

Marston, "FET Principles and Circuits," Part 1, *Nuts and Volts Magazine*, May 2000; 4 pgs.
Marston, "FET Principles and Circuits," Part 2, *Nuts and Volts Magazine*, Jun. 2000; 3 pgs.
Marston, "FET Principles and Circuits," Part 3, *Nuts and Volts Magazine*, Jul. 2000; 3 pgs.
Marston, "FET Principles and Circuits," Part 4, *Nuts and Volts Magazine*, Aug. 2000; 3 pgs.

* cited by examiner

*Primary Examiner* — Scott Getzow
*Assistant Examiner* — Amanda Patton
(74) *Attorney, Agent, or Firm* — Carol F. Barry

(57) ABSTRACT

A constant current pacing apparatus and method for pacing uses, for example, H-bridge circuitry and a constant current source connected to the H-bridge circuitry. Further, for example, protection is provided from high voltage pulses applied to the patient via one or more other medical devices.

10 Claims, 8 Drawing Sheets

US 8,452,399 B2

CONSTANT CURRENT PACING APPARATUS WITH PROTECTION FROM HIGH VOLTAGE PULSES

This application claims the benefit of U.S. Provisional Application Ser. No. 61/219,642 filed 23 Jun. 2009, entitled "CONSTANT CURRENT PACING APPARATUS AND PACING METHOD," and U.S. Provisional Application Ser. No. 61/219,652 filed 23 Jun. 2009, entitled "CONSTANT CURRENT PACING APPARATUS WITH PROTECTION FROM HIGH VOLTAGE PULSES," both of which are incorporated herein by reference in their respective entireties.

BACKGROUND

The disclosure herein relates generally to medical devices and, more particularly, to pacing circuitry and methods of pacing.

A variety of medical devices have been described which deliver a therapy to patients. For example, some medical devices are entirely or primarily located external to the body of a patient, while others are implantable in a patient. Some medical devices may use stimulation electrodes, sense electrodes, or other apparatus to deliver such therapy to a patient (e.g., deliver pacing or electrical stimulation to, the heart, muscle, nerve, brain, stomach, or other organs or tissue). For example, medical leads are configured to allow electrodes or sensors to be positioned at desired locations for delivery of stimulation or sensing (e.g., those having a proximal portion connected to medical device housing with a distal portion having electrodes or sensors located thereon). Other electrodes or sensors may be located on or within the medical device housing, or have a wireless connection to the system.

Cardiac pacemakers or cardioverter-defibrillators, for example provide therapeutic electrical stimulation to the heart via electrodes, e.g., electrodes carried by one or more leads. The electrical stimulation may include signals such as pulses or shocks for pacing, cardioversion or defibrillation. In some cases, a medical device may sense intrinsic depolarizations of the heart, and control delivery of stimulation signals to the heart based on the sensed depolarizations. For example, upon detection of abnormal rhythm, such as bradycardia, an appropriate electrical pacing stimulation signal or signals may be delivered to maintain or restore a normal rhythm. In other cases, for example, a medical device may deliver rapid pacing pulses to the heart of the patient upon detecting an abnormal rhythm, such as tachycardia. Still further, high voltage shocks may also be delivered for purpose of cardioversion of a tachycardia, or for defibrillation of the heart upon detecting fibrillation.

Further, medical device equipment may also be used to conduct temporary cardiac pacing. For example, such cardiac pacing may be performed at the end of an operative procedure, such as open heart surgery. External or temporary pulse generators (e.g., external pacemakers) are electronic devices packaged for control of the stimulation and to be located outside the patient's body. Examples of temporary or external pulse generators include, for example, the Medtronic Single-Chamber Model 5348 External Pulse Generator, and the Medtronic Dual-Chamber Model 5388 External Pulse Generator. For example, cardiac pacing leads may be attached to the patient's heart and be connected to an external pulse generator (EPG) for delivery of stimulation to the patient's heart. Various types of pacing leads, such as heart wires, are used to provide connection of the external pulse generator to the patient.

In one or more conventional types of pulse generators, such as external pulse generators, a constant current output is used for pacing. A constant current circuit is used that varies the output voltage to obtain a fixed output current regardless of lead impedance. One type of constant current circuit uses a current mirror transistor pair to deliver the output current. However, designing a constant current circuit using a current mirror may be challenging in that it can be difficult to match transistors to obtain equal current balancing in the circuit. Further, for example, accurately generating a low current bias signal (e.g., typically required in such circuits) in an efficient and noise immune manner is difficult. Still further, for example, many constant current designs use some sort of defibrillation protection, however, in some cases damage can still be caused by a defibrillation pulse directly applied to a patient in parallel with the device.

SUMMARY

The disclosure herein relates generally to apparatus that provides constant current pacing circuitry, and methods for providing pacing using such circuitry. For example, in one or more embodiments, a constant current pacing apparatus may include a constant current source connected to the high side or the low side of an H-bridge circuit (e.g., an H-bridge circuit for use in providing pacing and/or providing defibrillation protection).

One exemplary constant current pacing apparatus described herein (e.g., that may be part of an external pulse generator, or any other medical device) includes an H-bridge circuit that includes a high side and a low side (e.g., the H-bridge circuit includes first and second legs connected between the high side and low side thereof, wherein the first leg of the H-bridge circuit includes first and second current switching elements and the second leg of the H-bridge circuit includes at least a third current switching element, and wherein a patient is connectable to the first leg of the H-bridge circuit between the first and second current switching elements and to the second leg of the H-bridge circuit). One of the first and second current switching elements along with the third current switching element define a pair of current switching elements such that, when, for example, the constant current pacing apparatus is operational and the pair of current switching elements are selected, a pacing stimulus having a first polarity is applied to the patient. Further, each switching element of the H-bridge circuit may be associated with a diode (e.g., a body diode associated with a field effect transistor). The apparatus further includes a constant current source connected to the high side or the low side of the H-bridge circuit, wherein, the constant current source, when the constant current pacing apparatus is operational, applies a constant current output to the H-bridge circuit. A diode is connected between the constant current source and the H-bridge circuit to prevent external current flow from the H-bridge circuit to the constant current source. Further, the diodes associated with the current switching elements (e.g., body diodes associated with field effect transistors) of the H-bridge circuit and the diode connected between the constant current source and the H-bridge circuit protect the constant current pacing apparatus from high voltage pulses applied to the patient via one or more other medical devices.

One exemplary method of providing constant current pacing to a patient includes providing an H-bridge circuit including a high side and a low side (e.g., wherein the H-bridge circuit includes first and second legs connected between the high side and low side thereof, wherein the first leg of the H-bridge circuit includes first and second current switching elements and the second leg of the H-bridge circuit includes at least a third current switching element, and further wherein a patient is connectable to the first leg of the H-bridge circuit between the first and second current switching elements and to the second leg of the H-bridge circuit). One of the first and second current elements along with the third current switching element define a pair of current switching elements such that, when the constant current pacing apparatus is operational and the pair of current switching elements are selected, a pacing stimulus having a first polarity is applied to the patient. Further, the method includes providing a constant current source connected to the high side or the low side of the H-bridge circuit. A diode is connected between the constant current source and the H-bridge circuit. The constant current source is controlled to generate a constant current output to be applied to the H-bridge circuit for application of a pacing stimulus to the patient upon selection of the pair of current switching elements. The method further includes using the diodes associated with each current switching element of the H-bridge circuit and the diode, connected between the controlled current output circuit and the H-bridge circuit, to provide protection from high voltage pulses applied to the patient via one or more other medical devices.

The above summary is not intended to describe each embodiment or every implementation of the present disclosure. A more complete understanding will become apparent and appreciated by referring to the following detailed description and claims taken in conjunction with the accompanying drawings.

Figure 1:
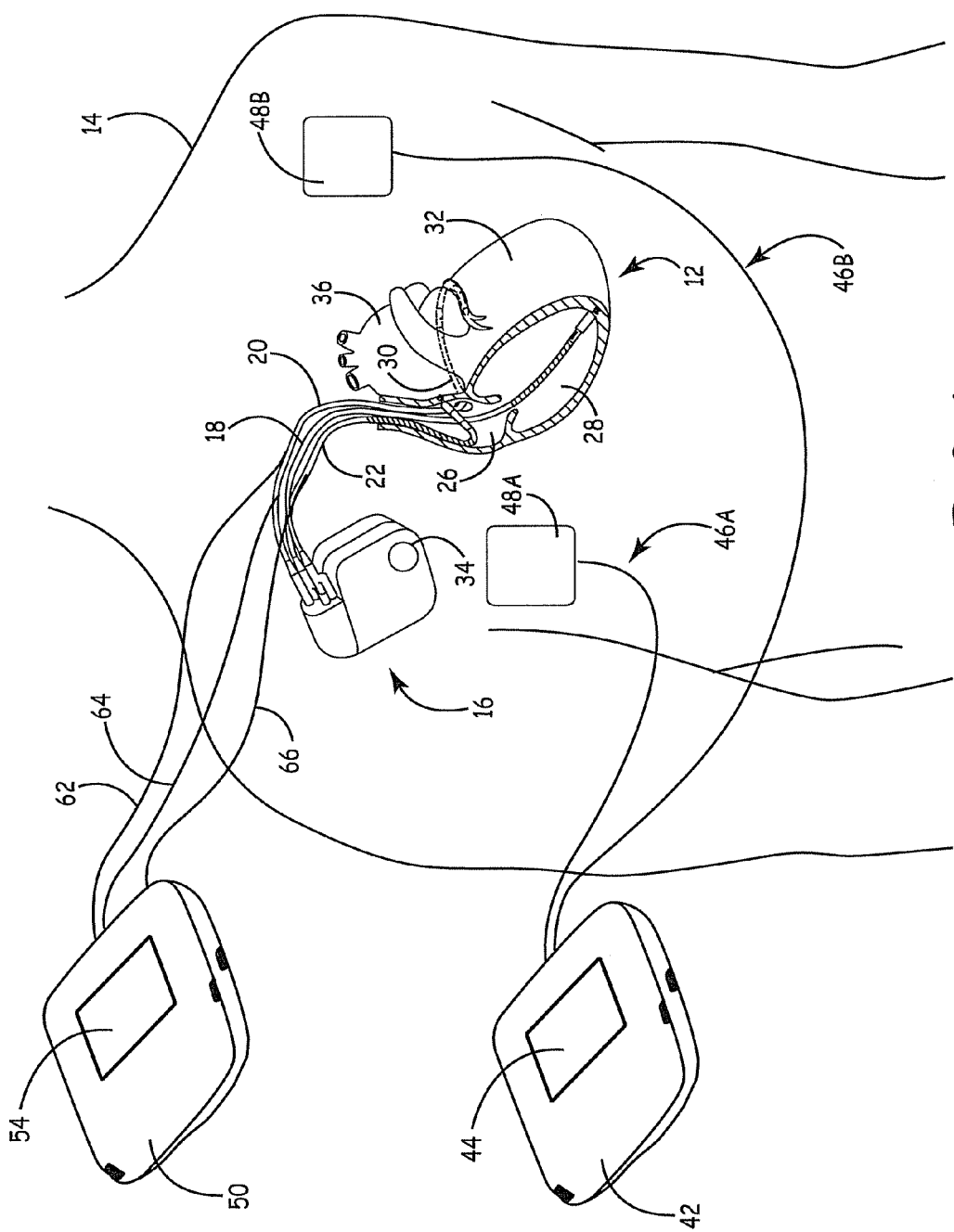
FIG. 1 is an illustrative drawing showing an example of an implantable cardiac device (ICD), an external pulse generator (EPG), and an external defibrillator device connected to a patient.

The figures are rendered primarily for clarity and, as a result, are not necessarily drawn to scale.

DETAILED DESCRIPTION OF EXEMPLARY EMBODIMENTS

In the following detailed description of illustrative embodiments, reference is made to the accompanying figures of the drawing which faun a part hereof, and in which are shown, by way of illustration, specific embodiments which may be practiced. It is to be understood that other embodiments may be utilized and structural changes may be made without departing from (e.g., still falling within) the scope of the disclosure presented hereby.

FIG. 1 is an illustrative drawing showing an example of an implantable cardiac device (ICD) 16, an external pulse generator (EPG) 50, and an external defibrillator device 42 connected to a patient 14. For example, the external defibrillator device 42 may be an automated external defibrillator, or a more fully featured external defibrillator. The exemplary external defibrillator device 42 is coupled to two electrodes 48A and 48B (collectively electrodes 48) that are applied to the surface, e.g., skin, of patient 14. Electrodes 48 are connected to defibrillator device 42 by respective leads or cables 46A and 46B (collectively cables 46). External defibrillator device 42 may detect electrical activity of the heart 12 of patient 14 via electrodes 48, and/or deliver electrical stimulation to the heart 12 via electrodes 48. For example, defibrillator device 42 may detect tachyarrhythmia and deliver one or more responsive defibrillation pulses to patient 14 via electrodes 48. As shown in FIG. 1, defibrillator device 42 includes a display 44, which may display an electrocardiogram generated based on the electrical activity detected by electrodes 48 via display 44. Other configurations of the defibrillator device 42 and/or leads and electrodes thereof (e.g., number and position of the leads and electrodes) are possible and the disclosure herein is not limited to any particular configuration.

Further, for example, the ICD 16 may be used to monitor and deliver therapy to heart 12 of patient 14. For example, in one or more embodiments, the ICD 16 is coupled to leads 18, 20, and 22. ICD 16 may deliver electrical signals to heart 12 and sense electrical signals attendant to the depolarization and repolarization of heart 12 via electrodes (not shown) coupled to one or more leads 18, 20, and 22 and, in some cases, a housing electrode (not shown) of ICD 16. ICD 16 may operate as an implantable pacemaker, a cardioverter, and/or a defibrillator. For example, right ventricular (RV) lead 18 may extend through one or more veins (not shown), the superior vena cava (not shown), and right atrium 26, and into right ventricle 28. Left (LV) coronary sinus lead 20 may extend through one or more veins, the vena cava, right atrium 26, and into the coronary sinus 30 to a region adjacent to a wall of the left ventricle 32 of the heart 12. Right atrial (RA) lead 22 may extend through one or more veins and the vena cava, and into the right atrium 26 of the heart 12. Other configurations of the ICD and/or leads thereof (e.g., number and position of the leads) are possible and the disclosure herein is not limited to any particular configuration.

Further, for example, the EPG 50 (e.g., an external or temporary pacemaker) may be used to monitor and deliver therapy to heart 12 of patient 14. For example, in one or more embodiments, the EPG 50 is coupled to leads 62, 64, and 66 (which for illustration purposes only are the same as leads 18, 20, and 22, as they could be the same or different leads). EPG 50 may be any external or temporary pulse generator packaged for control of stimulation and be located outside the patient's body. Examples of temporary or external pulse generators include, for example, the Medtronic Single-Chamber Model 5348 External Pulse Generator, and the Medtronic Dual-Chamber Model 5388 External Pulse Generator. For example, the cardiac pacing leads 62, 64, and 66 may be attached to the patient's heart and be connected to an external pulse generator (EPG) for delivery of stimulation to the patient's heart. Other configurations of the EPG and/or leads and electrodes thereof (e.g., number and position of the leads/electrodes) are possible and the disclosure herein is not limited to any particular configuration. For example, in many EPGs, either two or four leads are used.

After an electrical pulse is delivered to the heart, the heart may be monitored to determine the condition of the patient (e.g., using the ICD or EPG). For example, one may monitor the heart to determine if pacing resulted in a particular response (e.g., an evoked response indicative of capture or non-capture) to determine if the therapy delivered was effective, and, if not, to deliver additional therapy (e.g., more of the same stimulation or a modified stimulation). For example, one or more sense amplifier circuits receiving cardiac signals along with circuitry for processing such signals may be used to monitor the heart, such as described, for example, in U.S. Pat. No. 5,861,013, to Peck et al., entitled "Peak Tracking Capture Detection Circuit and Method," issued Jan. 19, 1999, which is incorporated herein in its entirety.

Although various devices may be used together for a patient, in some examples, the devices may not be configured to communicate with each other. As such, for example, the EPG 50 (or ICD 16) and the external defibrillator 42 may not operate in a coordinated fashion and, thus, the EPG 50 may be exposed to high voltages when the external defibrillator 42 is being used to deliver therapy to the heart 12.

Figure 2:
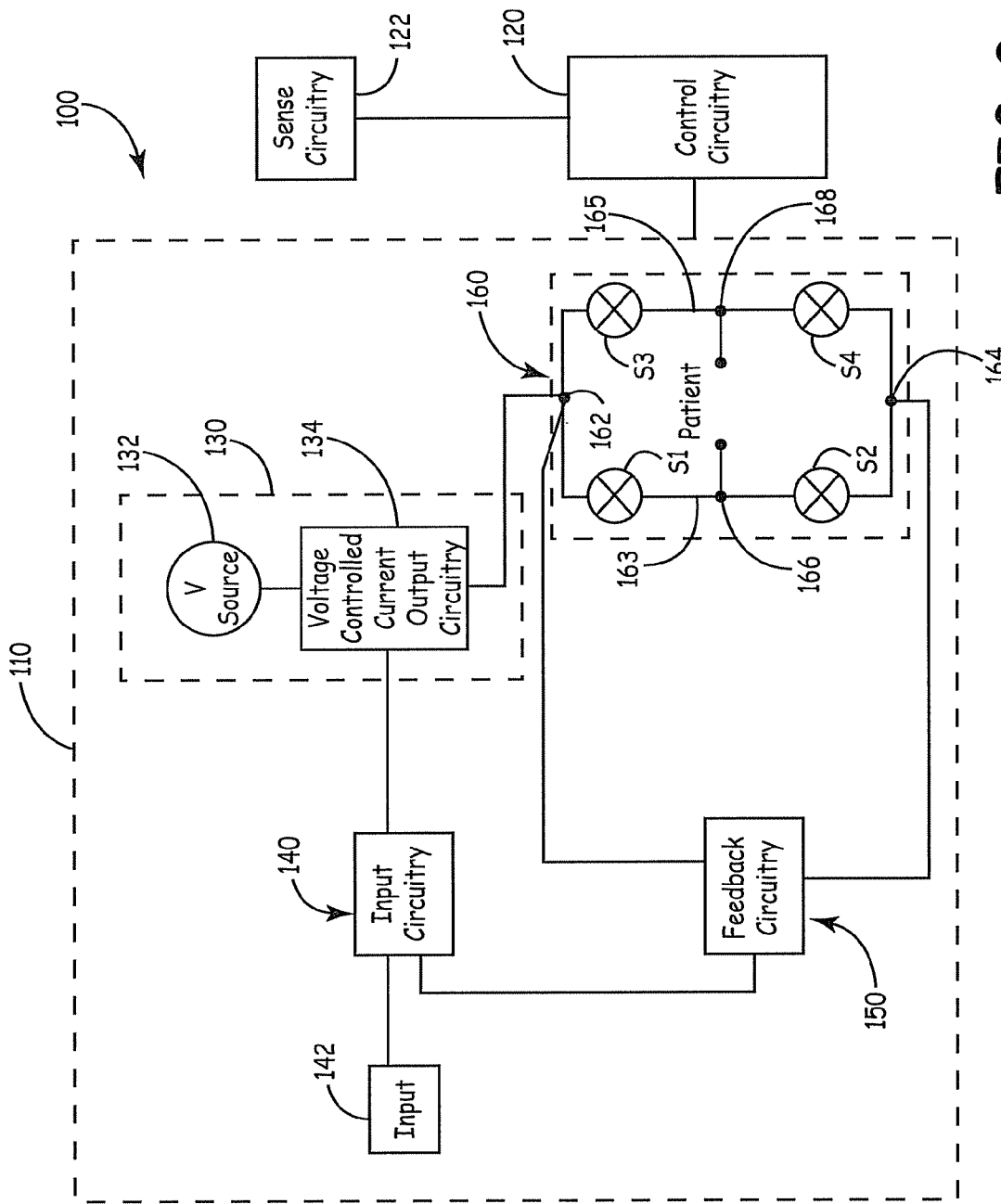
FIG. 2 is an illustrative functional block diagram of an exemplary constant current pacing apparatus, such as for use, for example, in an EPG.

In one or more embodiments described herein, EPG 50 (or any other medical device) may use a constant current pacing apparatus 100 such as shown in FIG. 2 to provide a constant current output for providing stimulation (e.g., pacing of heart 12). A constant current pacing apparatus (e.g., such as apparatus 100) will vary the output voltage to obtain a fixed output current regardless of lead impedance. As described herein, in one or more embodiments, a device operable in a linear mode (e.g., a FET operating in linear mode) is used to deliver an arbitrary waveform constant current pacing output. One or more embodiments of the constant current pacing apparatus provide an improved signal to noise ratio allowing for greater accuracy. In one or more embodiments, microprocessor driven digital to analog conversion is used to generate the arbitrary waveform to be applied to the input of the constant current pacing apparatus such that scaled micro-amp accuracy can be achieved. Further, in one or more embodiments, high voltage defibrillation protection is provided by the constant current pacing apparatus such that the pacing circuitry is protected from high voltage (e.g., 1000 volt) defibrillation pulses that, for example, may be applied by the external defibrillator device 42 (e.g., which may not be configured to operate together with the EPG 50).

Still further, in one or more embodiments, the constant current pacing apparatus may have the ability to deliver an active recharge pulse that will more quickly remove lead polarization upon delivery of a stimulation pulse (e.g., more quickly remove the DC polarization of the tissue electrode interface following a therapy pacing pulse being applied). For example, quickly removing such polarization allows for the implementation of evoked response detection (e.g., allowing for automatic pacing output threshold detection to improve ease of use of the EPG, allow for the arbitrary waveform to be modified, etc.). Yet further, one or more embodiments of the constant current pacing apparatus can be used to deliver any analog waveform shape for pacing that would allow for exploration, for example, of an optimal low power wave shape for pacing capture and sub-threshold impedance measurements.

Although the constant current pacing apparatus 100 as shown in FIG. 2 is described with respect to use in an EPG, the constant current pacing apparatus 100 or portions thereof may be used in one or more other medical devices, such as, for example, an implantable medical device used in a body near a human heart (e.g., any implantable cardiac pacemaker, defibrillator, cardioverter-defibrillator, or pacemaker-cardioverter-defibrillator (PCD)). Further, for example, the constant current pacing apparatus 100, or portions thereof, may be used in one or more other medical devices such as a nerve stimulator or muscle stimulator, a monitoring device (e.g., a hemodynamic monitoring device), a brain stimulator, a gastric stimulator, a drug pump, or any other device (e.g., implantable or external) that would benefit from one or more of the advantages provided thereby. Therefore, the apparatus 100 or portions thereof may find wide application in any form of medical device. As such, any description herein making reference to any particular medical device is not to be taken as a limitation of the type of medical device which can benefit from and which can employ the circuitry described herein. However, some medical devices may benefit more than others by the use thereof.

One exemplary embodiment of the constant current pacing apparatus 100 is illustrated in the functional block diagram of FIG. 2. As shown therein, the constant current pacing apparatus 100 may include constant current pacing circuitry 110 coupled to control circuitry 120 (e.g., a controller, such as a processing apparatus and associated software and hardware to perform one or more functions).

Further, for example, sense circuitry 122 is also coupled to controller 120. For example, sense circuitry 122 may include one or more sense amplifier circuits receiving cardiac signals to monitor the heart (e.g., sense evoked responses of the heart), such as described, for example, in U.S. Pat. No. 5,861, 013, to Peck et al., or, for example, in U.S. Pat. No. 5,117,824, to Keimel et al., entitled Apparatus For Monitoring Electrical Physiologic Signals" issued Jun. 2, 1992, incorporated by reference herein in their entirety.

The control circuitry 120 may include any type of circuitry used to control, for example, the constant current pacing circuitry 110 and/or other portions of the medical device with which it is used. For example, the control circuitry 120 is generally representative of a processor and associated memory. The memory, for example, may include computer readable instructions that, when executed by processor, cause the constant current pacing circuitry 110 and or any other component of the medical device with which the constant current pacing circuitry 110 is used to perform various functions attributed to them. For example, the memory may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

The processor, may include any one or more of a microprocessor, a digital signal processor (DSP), a controller, an application specific integrated circuit (ASIC), a field programmable gate array (FPGA), or equivalent discrete or integrated logic circuitry. In one or more exemplary embodiments, the processor may include multiple components, such as any combination of one or more microprocessors, one or more controllers, one or more DSPs, one or more ASICs, or one or more FPGAs, as well as other discrete or integrated logic circuitry. The functions attributed to the control circuitry 120 may be embodied as software, firmware, hardware, or any combination thereof.

The control circuitry 120 controls the delivery of stimulation to patient 14 coupled to the constant current pacing circuitry 110. In the exemplary embodiment shown in FIG. 2, the constant current pacing circuitry 110 includes input circuitry 140 for receiving at least an input signal 142 (e.g., a shaped waveform or a static DC level signal proportional to the desired pacing amplitude), a constant current source 130, and one or more H-bridge circuits 160, and feedback circuitry 150. For example, the control circuitry 120 controls the constant current pacing circuitry 110 to deliver stimulation therapy, e.g., pacing, to heart 12 of patient 14 based on a selected one or more therapy programs, which may be stored in memory.

As generally represented by the dashed block about the H-bridge circuit 160, one or more H-bridge circuits may be used in the constant current pacing circuitry 110. For example, each H-bridge circuit may be connected to a patient as described herein to provide stimulation at one or more different locations of the heart. For example, a first H-bridge circuit may be used to pace the left ventricle, a second H-bridge circuit may be used to pace the right ventricle, and a third H-bridge circuit may be used to pace the right atrium for biventricular pacing. It may also be possible to pace or measure impedance between H-bridges. Control circuitry 120, for example, would control the constant current pacing circuitry 110 having three H-bridge circuits to deliver biventricular pacing, e.g., pacing, to heart 12 of patient 14 utilizing a selection of appropriate switches of the H-bridge circuits. For simplicity, the main portion of description provided herein will focus on use of a single H-bridge circuit, although more than one H-bridge circuit may be used and controlled to provide any number of stimulation therapies.

Each H-bridge circuit 160, as shown in the exemplary embodiment of FIG. 2, includes a high side 162 and a low side 164. Further, for example, the H-bridge circuit 160 includes first and second legs 163, 165 connected between the high side 162 and low side 164 thereof. The first leg 163 of the H-bridge circuit 160 includes first and second current switching elements S1, S2 and the second leg 165 of the H-bridge circuit 160 includes third and fourth current switching elements S3, S4. The first current switching element S1 is connected towards the high side 162 of the H-bridge circuit 160 and the second current switching element S2 is connected towards the low side 164 of the H-bridge circuit 160. Further, the third current switching element S3 is connected towards the high side 162 of the H-bridge circuit 160 and the fourth current switching element S4 is connected towards the low side 164 of the H-bridge circuit 160. In one or more embodiments as described herein, the H-bridge circuit 160 may include only three current switching elements (e.g., such as when a passive recharge is used to remove DC polarization at the tissue/electrode interface). For example, in one or more embodiments, switching element S1 or S3 may be eliminated at the high side 162 of the H-bridge circuit 160 (or in one or more embodiments, switching element S2 or S4 at the low side 164 may be eliminated).

A patient is connectable (e.g., using leads/electrodes and any other suitable connections) between a first node 166 of the H-bridge circuit 160 located between the first and second current switching elements S1, S2 and a second node 168 of the H-bridge circuit 160 located between the third and fourth current switching elements S3, S4. In one or more embodiments, wherein only three current switching elements are used in the H-bridge circuit 160 (e.g., S3 eliminated), a patient is connectable to the first leg 163 of the H-bridge circuit 160 between the first and second current switching elements S1, S2 and to the second leg of the H-bridge circuit 160 (e.g., to the fourth current switching element S4). In one or more exemplary embodiments, when the constant current pacing apparatus 100 is operational under control of control circuitry 120, and the first and fourth current switching elements S1, S4 are selected, a pacing stimulus having a first polarity is applied to the patient 14. Further, for example, in one or more embodiments, when the constant current pacing apparatus 100 is operational under control of control circuitry 120, and the second and third current switching elements S2, S3 are selected, a stimulus having a second polarity is applied to the patient 14 (e.g., to provide active recharge). As described further herein, selection of one or more of the switches under control of control circuitry 120 may be used to provide one or more functions. For example, selection of certain switches in one or more configurations of the constant current pacing apparatus 100 may be used to provide one or more types of stimulation pulses, may be used to provide active or passive recharge, etc.

For example, in one or more embodiments, various pairs of switches may be used to provide one or more functions described herein. For example, when the H-bridge circuit 160 includes current switching elements S1-S4, one of the first and second current switching elements S1, S2 along with one of the third and fourth current switching elements S3, S4 may define a first pair of current switching elements such that, when the constant current pacing apparatus 100 is operational and the first pair of current switching elements (e.g., S1 and S4) are selected, a pacing stimulus having a first polarity may be applied to the patient 14. Further, the other current switching elements S2 and S3 may also define a second pair of current switching elements such that, when the constant current pacing apparatus 100 is operational and the second pair of current switching elements are selected, an active recharge of a second polarity may be applied to the patient 14. One will recognize that either of the pairs may be used to provide either the first or early phase of the pacing cycle or the active recharge or late phase thereof.

Further, for example, when only three current switching elements are used in the H-bridge circuit 160 (e.g., S3 eliminated), selecting a first pair of current switching elements (e.g., S1 and S4) may provide for a pacing stimulus having a first polarity to be applied to the patient 14. Further, the selection of current switching elements S2 and S4 may also define a pair of current switching elements such that when this pair of current switching elements are selected a passive recharge may be performed as described herein. As will be recognized, the switches selected may depend on the configuration of the H-bridge circuit (e.g., whether three or four current switching elements are being used, whether connection is to the high side or low side, etc.). For example, if S4 is eliminated at the low side, then the passive recharge could occur with selection of S1 and S3.

As shown in FIG. 2, the constant current pacing apparatus 100 further includes the constant current source 130 connected to the high side 162 of the H-bridge circuit 160. However, one will recognize that the constant current source 130 may be connected to the low side 164 of the H-bridge circuit 160 and could be either positive or negative in polarity. In the exemplary embodiment shown in FIG. 2, the constant current source 130 includes a voltage source 132 and a controlled current output circuit 134 connected between the voltage source 132 and the high side 162 of the H-bridge circuit 160. The controlled current output circuit 134 includes one or more devices that define a proportional relationship between the control signal applied thereto and the constant current output applied to the H-bridge circuit 160. For example, the controlled current output circuit 134 may include a circuit that includes a current limiting function. In one or more embodiments, the controlled current output circuit 134 includes a device operable in a linear mode such that, when the constant current pacing apparatus 100 is operational, application of a control signal (e.g., a control voltage) thereto representative of a pacing stimulus to be applied to the patient 14 results in a constant current output applied to the high side 162 of the H-bridge circuit 160 based on a defined relationship between the control signal and the constant current output.

In one or more embodiments, other current sources such as a current mirror or other constant current source (e.g., using a current transformer) may be used (e.g., with an H-bridge circuit to provide defibrillation protection).

The voltage source 132 may be provided in any suitable manner. For example, the voltage source may be programmable or static, the voltage source may be provided by one or more batteries, the voltage source may be a switched or linear regulated source, etc.

The device operable in a linear mode may be any device that provides a proportional relationship between the control voltage and the constant current output. The device may include any number of circuit components to provide the relationship. In one or more embodiments of the controlled current output circuit 134, the device operable in a linear mode may include a transistor (e.g., a field effect transistor) operating in a non-saturation mode (e.g., a linear mode), wherein application of a gate to source control voltage above the threshold voltage of the device results in a constant source current output based on the gate to source control voltage applied thereto. One will recognize that other devices which provide a proportional relationship between the control signal and current output may be used. For example, an insulated gate bipolar transistor (IGBT), or any other transistor that can operate in a non-saturation mode may be used as part of the constant current source 130.

Figure 7:
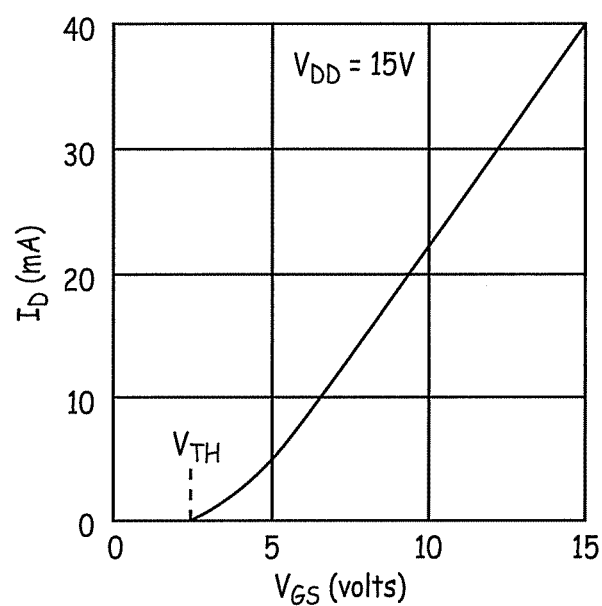
FIG. 7 is a graph illustrating typical $V_{GS}/I_D$ characteristics of an n-channel enhancement-mode MOSFET device.

Further, for example, in one or more embodiments, the field effect transistor may include an n-channel MOSFET enhancement mode device. For example, FIG. 7 shows a graph illustrating typical $V_{GS}/I_D$ characteristics of an n-channel enhancement-mode MOSFET device (i.e., the current flowing through the drain ($I_D$) also being the current flowing through the source ($I_S$)). As noted in FIG. 7, upon $V_{GS}$ exceeding the $V_{TH}$ of the device, a generally proportional relationship (e.g., linear in at least a portion of the relationship) exists between $V_{GS}$ and $I_D$ when operating in the linear mode (sometimes referred to as operating in the triode region, or in other words in the non-saturation region after the threshold of the device is met) which allows the constant current output of the constant current source 130 to follow the $V_{GS}$ in a proportional relationship. For example, a static $V_{GS}$ applied results in a static constant current output while a varied $V_{GS}$ applied results in a constant current output that follows the variation of $V_{GS}$ (e.g., the FET operates somewhat like a variable resistor in the linear mode based on the defined relationship between $V_{GS}/I_D$).

As shown in the exemplary embodiment of FIG. 2, the input circuitry 140 of the constant current pacing apparatus 100 drives the constant current source 130 connected to the high side 162 of the H-bridge circuit 160, or in other words, in one exemplary embodiment, applies a control voltage representative of the pacing stimulus to be delivered to a patient to the voltage controlled current output circuit 134 (e.g., applies a $V_{GS}$ to an n-channel enhancement-mode MOSFET device that results in a constant source current output). The input circuitry 140 may include any circuitry suitable to receive an arbitrary input waveform 142 representative of the pacing stimulus to be delivered to a patient and drive the controlled current output circuit 134.

In the exemplary embodiment of FIG. 2, the input circuitry 140 may also include any circuitry suitable to receive a feedback input signal from feedback circuitry 150 representative of a pacing stimulus previously applied to a patient 14. The feedback circuitry 150 along with the input circuitry 140 provide a feedback controlled loop for use in controlling application of the control voltage to the constant current source 130.

In one or more embodiments, for example, the input circuitry 140 may include one or more operational amplifiers, or any other suitable circuitry, to receive an arbitrary input voltage waveform representative of a stimulus signal to be applied to a patient and a voltage feedback input signal representative of the pacing stimulus previously applied to the patient for use in providing a control voltage output for application to the constant current source 130. For example, feedback circuitry 150 may include one or more sense amplifiers for use in sensing current flow to the patient 14. The one or more sense amplifiers may operate as current to voltage converting feedback circuitry to sense the current applied to the patient and provide a voltage feedback input signal to the input circuitry 140. The feedback controlled loop may include filter circuitry (e.g., as part of the input circuitry or feedback circuitry) defining a dominant pole of the controlled feedback loop to provide dominant pole compensation (e.g., a dominant pole filter may be connected at the output of the operational amplifier of the input circuitry, or a dominant pole may be provided by the amplifier configurations of the input or feedback circuitry). Further, the input circuitry 140 provides suitable gain and/or other signal conditioning.

Further, for example, the feedback circuitry 150 may include voltage sense circuitry to sense voltage across a connected patient 14 and the current sense circuitry to sense current flow applied to a connected patient 14. For example, the control circuitry 120 may sample both a voltage sense signal representative of voltage across a connected patient 14 and a current sense signal representative of current flow applied to a connected patient 14. The control circuitry 120 (e.g., processing circuitry) may then determine lead impedance from the sample voltage sense signal and current sense signal (e.g., sensed voltage/sensed current). Such lead impedance, for example, may be used to determine if a lead has been dislodged or damaged (e.g., determine if a short or open is present in the circuit, determine if certain limits have been exceeded, etc.), or detection of the absence of a lead could be used to change pacing modes or limit pacing mode selections.

The arbitrary input signal 142 (e.g., a shaped waveform or a static DC level signal) applied to the input circuitry 140 (e.g., a waveform or static DC level signal between 0 to 2.5 volts) representative of the stimulus to be applied to the patient (e.g., via a constant current output in the range of 0 to 25 mA) may be generated in any suitable manner. For example, in one or more embodiments, the arbitrary input waveform 142 is a voltage waveform generated using a microprocessor driven digital to analog conversion. Using such a microprocessor driven digital to analog conversion allows high accuracy scaling of input voltage to desired constant current output.

Further, for example, input signals, other than digital to analog converted signals, may be used (e.g., those generated using analog circuitry). For example, a capacitor could be connected across an input waveform to ground and then be charged and discharged by other associated circuitry. The voltage created on the capacitor could be used as the input signal. Further, for example, a varying current could be applied to a resistor similarly connected so as to create a varying waveform for use as the input signal.

The arbitrary input signal 142 may be any input form desired for a particular application. For example, the arbitrary input may be a static DC level signal or a shaped waveform.

For example, an arbitrary input signal will differ depending on the function to be performed (e.g., the signal is different if pacing and active recharge is used as opposed to generation of a biphasic pacing stimulus or using passive recharge as described herein).

Figure 3A:
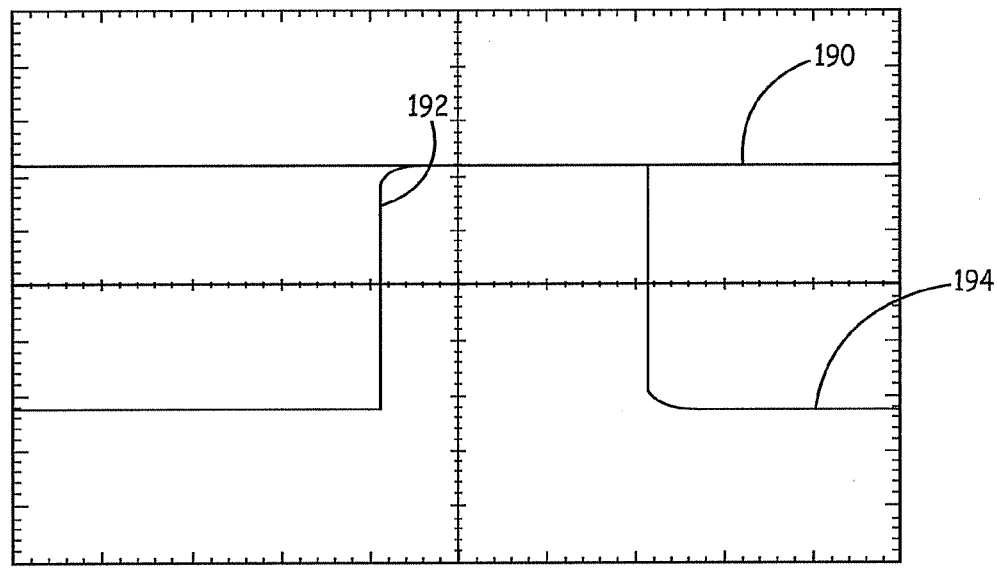
FIGS. 3A-3B are waveform diagrams illustrating arbitrary input waveforms and resulting delivered waveforms using, for example, a constant current pacing apparatus, such as functionally shown in FIG. 2.
Figure 3B:
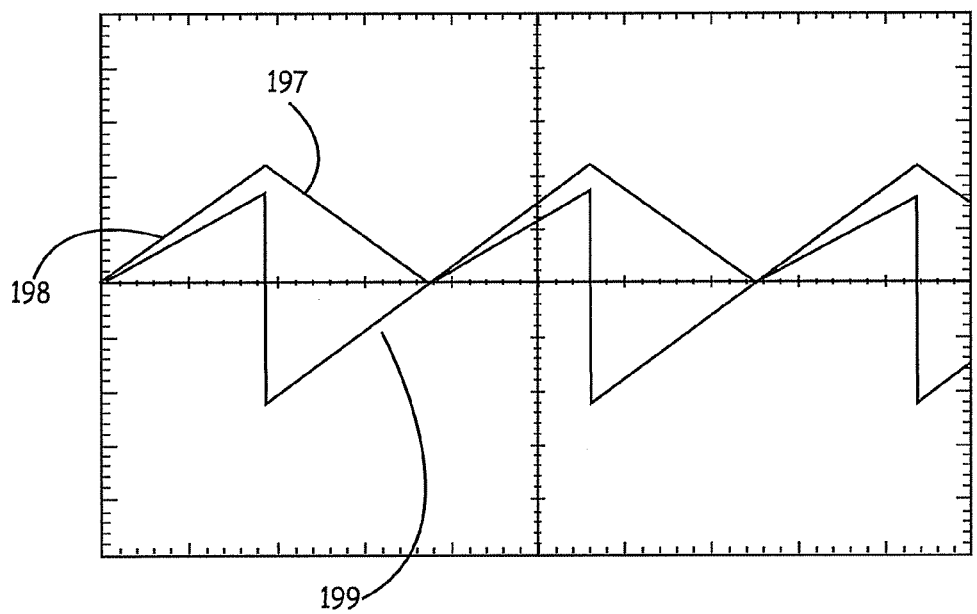

FIGS. 3A and 3B show diagrams illustrating arbitrary input signals (e.g., selected input waveforms) and resulting delivered waveforms using, for example, a constant current pacing apparatus 100, such as functionally shown in FIG. 2. As used herein, the term "arbitrary" input signal refers to the ability to select any shape of input (e.g., voltage waveform, static DC level input, shaped waveform, etc.) for use in generating a resulting current waveform (e.g., that generally follows the same shape (e.g., a ramped voltage input waveform being used to generate a ramped delivered current waveform, a static input used to deliver a proportional current, etc.)).

FIG. 3A shows use of a static input signal (e.g., a 1.5 V static input) for generating a proportional delivered waveform (e.g., measured across a 500 ohm load). In other words, for example, when the constant current pacing apparatus 100 is operational and a static input waveform 190 is applied to the input circuitry, and the first and fourth current switching elements S1, S4 are selected, a pacing stimulus or delivered waveform 192 having a first polarity (e.g., a positive polarity) is applied to the patient 14. Further, for example, when the constant current pacing apparatus 100 is operational with the static input waveform 190 being applied, and the second and third current switching elements S2, S3 are selected, a pacing stimulus or delivered waveform 194 having a second polarity (e.g., a negative polarity) is applied to the patient 14.

FIG. 3B shows use of a varied ramped input waveform 197 for generating a delivered waveform 198 (e.g., measured across a 500 ohm load). In other words, for example, when the constant current pacing apparatus 100 is operational with input waveform 197 applied to the input circuitry 140, and the first and fourth current switching elements S1, S4 are selected, a pacing stimulus or delivered waveform 198 having a first polarity (e.g., a positive polarity) is applied to the patient 14. Further, for example, when the constant current pacing apparatus 100 is operational with input waveform 197 applied to the input circuitry 140, and the second and third current switching elements S2, S3 are selected, a pacing stimulus or delivered waveform 199 having a second polarity (e.g., a negative polarity) is applied to the patient 14.

Figure 6:
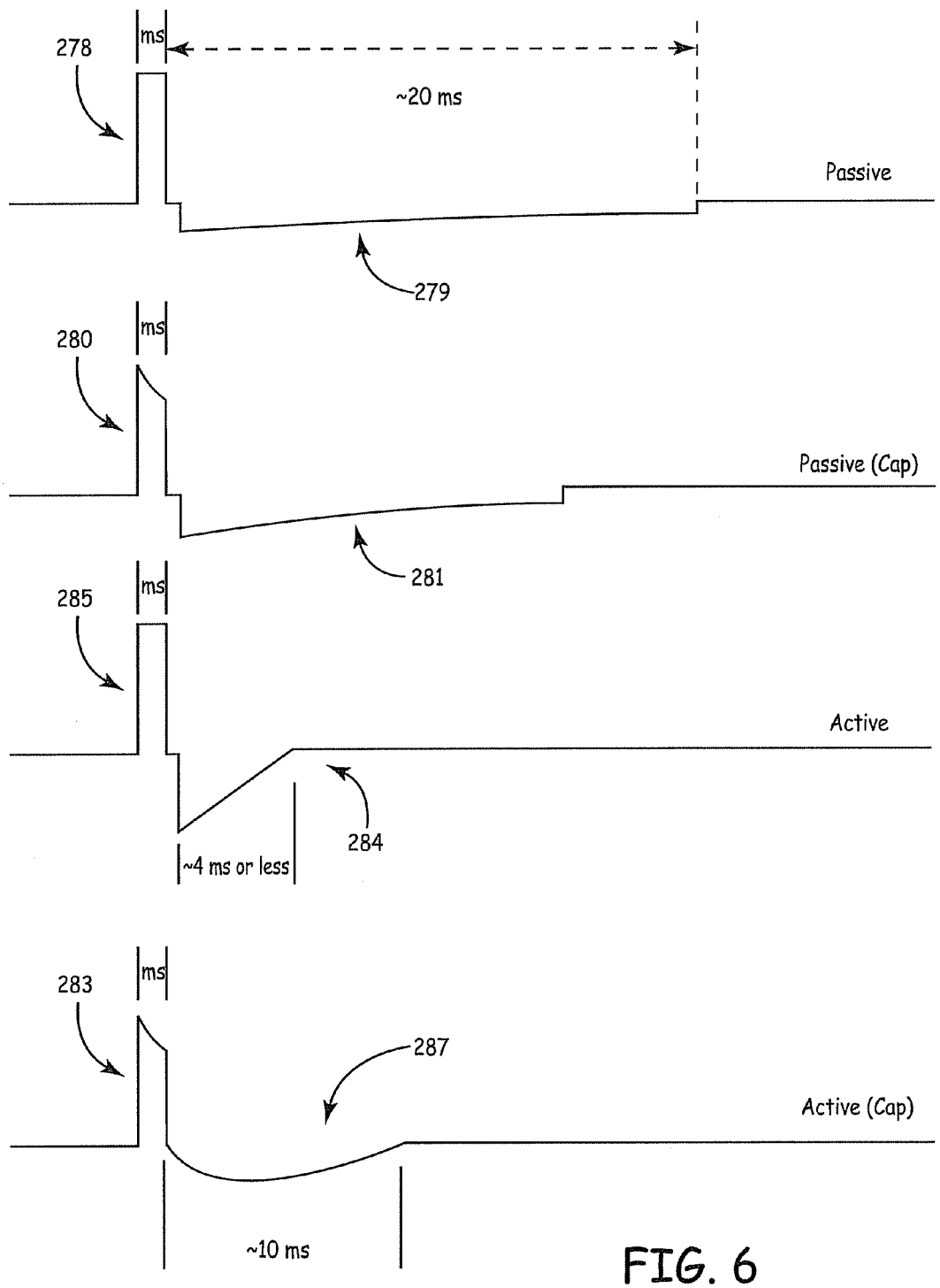
FIG. 6 is an exemplary timing diagram for use in illustrating one or more various methods of providing constant current pacing to a patient.

In other words, the constant current pacing apparatus 100 is suitable to provide any number of different arbitrary pacing waveforms for stimulus of a patient as shown in FIGS. 3A-3B. For example, in one or more embodiments, the control circuitry 120 may be configured to receive a signal representative of an evoked response to pacing stimuli applied to a patient (e.g., using sense circuitry 122) and modify the arbitrary input signal 142 based thereon (e.g., change the amplitude or shape of the pulse). Further, for example, in one or more embodiments, the control circuitry may be configured to provide stimulus using an arbitrary input waveform that includes a pacing pulse portion and an active recharge pulse portion as illustrated in FIG. 6 (e.g., wherein the active recharge pulse 284 is used to quickly remove lead polarization due to the pacing pulse portion, such that, for example, an evoked response to the pacing stimulus may be sensed using sense circuitry 122).

Figure 4A:
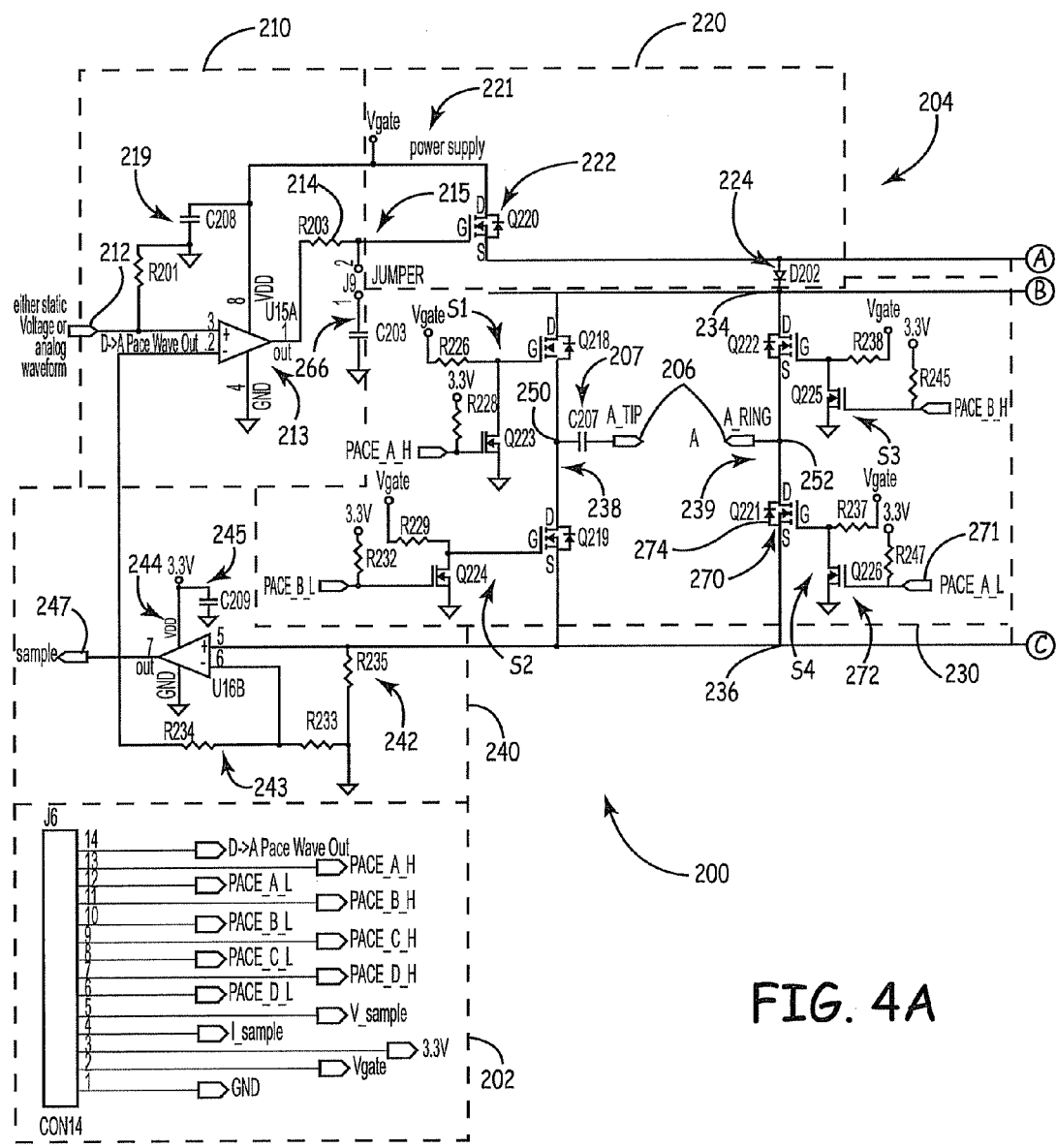
FIGS. 4A-4B (hereinafter referred to as FIG. 4) show an exemplary schematic diagram of a constant current pacing apparatus, such as functionally shown in FIG. 2.
Figure 4B:
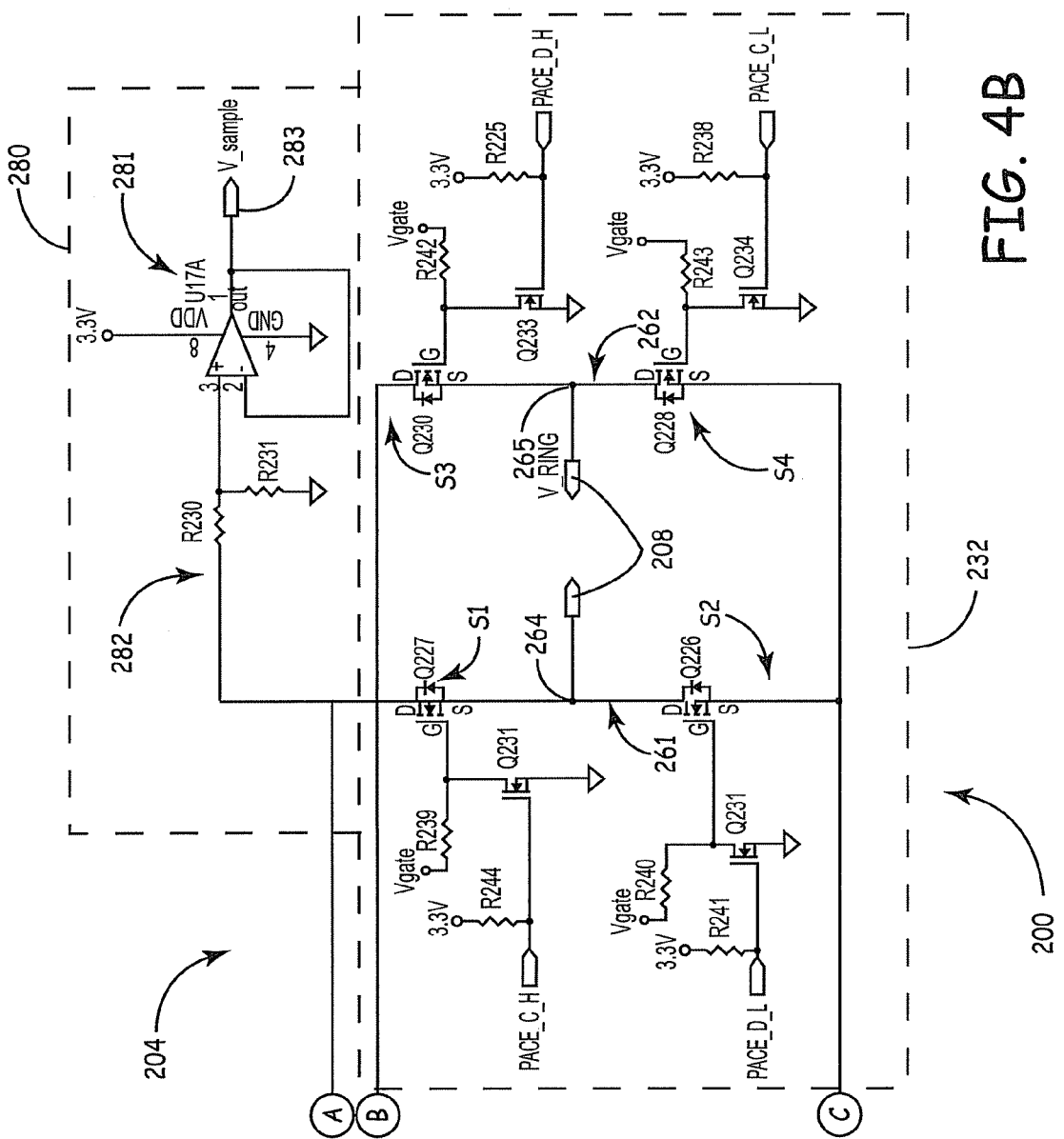

FIG. 4 shows an exemplary schematic diagram of a constant current pacing apparatus 200, such as functionally shown in FIG. 2. Control circuitry (generally shown as circuitry block 202) controls the delivery of stimulation to patient 14 coupled to the constant current pacing circuitry 204 by electrode pairs 206 and 208 (e.g., pairs of ring and tip electrodes). In the exemplary schematic diagram shown in FIG. 4, the constant current pacing circuitry 204 includes input circuitry 210 for receiving at least an input waveform 212 from control circuitry 202, a constant current source 220, two H-bridge circuits 230, 232, and feedback circuitry 240. For example, the control circuitry 202 controls the constant current pacing circuitry 204 to deliver stimulation therapy, e.g., pacing, to heart 12 of patient 14 based on a selected one or more therapy programs, which may be stored in memory. For example, control circuitry 202 provides control output signals for control of the H-bridge current switching elements (e.g., Pace_A_L to Pace_D_L for control of current switches of H-bridge 230 and Pace_A_H to Pace_D_H for control of current switches of H-bridge 232). Further, for example, control circuitry 202 provides the arbitrary input signal 212 (e.g., D to A Pace Wave Out) for application to input circuitry 210.

The H-bridge circuit 230, as shown in FIG. 4, is connected between a high side 234 and a low side 236. The other H-bridge circuit 232 is connected in parallel with the H-bridge circuit 230 between the high side 234 and low side 236. The only difference between the two H-bridge circuits is that H-bridge circuit 230 includes a capacitor 207 connected in series with the patient when a patient is connected to the H-bridge circuit 230. However, such a capacitor configuration may be used with any of the H-bridge circuits described herein or none of such H-bridge circuits and is further described herein.

The H-bridge circuit 230 includes first and second legs 238, 239 connected between the high side 234 and low side 236 thereof. The first leg 238 of the H-bridge circuit 230 includes first and second current switching elements S1, S2 and the second leg 239 of the H-bridge circuit 230 includes third and fourth current switching elements S3, S4. The first current switching element S1 is connected towards the high side 234 of the H-bridge circuit 230 and the second current switching element S2 is connected towards the low side 236 of the H-bridge circuit 230. Further, the third current switching element S3 is connected towards the high side 234 of the H-bridge circuit 230 and the fourth current switching element S4 is connected towards the low side 236 of the H-bridge circuit 230.

A patient is connectable to the first leg 238 of the H-bridge circuit 230 between the first and second current switching elements S1, S2 (e.g., first node 250) and to the second leg 239 of the H-bridge circuit 230 located between the third and fourth current switching elements S3, S4 (e.g., second node 252) by connections 206. When the constant current pacing apparatus 200 is operational under control of control circuitry 202, and the first and fourth current switching elements S1, S4 are selected, a pacing stimulus having a first polarity is applied to the patient 14 via electrodes 206 (e.g., electrodes provided by leads from an EPG to the heart). Further, for example, when the constant current pacing apparatus 200 is operational under control of control circuitry 202, and the second and third current switching elements S2, S3 are selected, a pacing stimulus having a second polarity is applied to the patient 14 via electrodes 206. Further, capacitor 207 is connected between the first and second nodes 250, 252 of the H-bridge circuit 230 and in series with the patient 14 when a patient is connected between the first and second nodes 250, 252 of the H-bridge circuit 230 (e.g., the capacitor may be used to provide a passive recharge as described herein with reference to FIG. 6—Passive (Cap) or an active recharge as described herein with reference to FIG. 6—Active (Cap)).

The H-bridge circuit 232 is substantially the same as H-bridge circuit 230 as indicated except for capacitor 207. As such, the H-bridge circuit 232 includes similar components such as current switching elements S1-S4 connected between the high side 234 and low side 236 along first and second legs 261, 262 of the H-bridge circuit 232 and a patient 14 is connectable between a first node 264 of the H-bridge circuit 232 located between the first and second current switching elements S1, S2 and a second node 265 of the H-bridge circuit 232 located between the third and fourth current switching elements S3, S4 by connections 208.

As shown in FIG. 4, each of the current switching elements S1-S4 are provided by substantially the same switch and control components (e.g., identical switching elements having a current blocking component associated therewith, such as a diode connected across the source and drain, a body diode, etc.). In one or more embodiments, any configuration for providing such current switching elements may be used and the disclosure herein is not limited by this particular configuration. Each of the current switching elements S1-S4 shown in FIG. 4 include a FET 270 as labeled for S4 (e.g., a high voltage N-channel enhancement mode MOSFET device) that is normally off, but turned on by application of $V_{GS}$ that is much higher than $V_{TH}$ of the device such that the device operates in the saturation region of the device (e.g., in this case the Vgate being much higher than the $V_{TH}$ of the device such that application of an "on" signal on PACE input signal line 271 turns on control FET 272 which in turn puts FET 270 into the saturation region of operation (e.g., the FET 270 is on). Further, each of the FETs of the current switching elements S1-S4 includes a source to drain diode (e.g., body diode 274 for blocking current in one direction) for providing high voltage protection as further described herein. One will recognize that, although FETs are used and described herein, one or more functions provided by such FETs may be implemented using other types of transistor devices (e.g., IGBTs) and that the present description is not limited to only the use of FETs or MOSFETs (as such, the term's, emitter and collector, may in such cases be substituted for the terms, source and drain).

Although each of the H-bridge circuits 230, 232 may be configured the same, or only one H-bridge circuit may be used as opposed to two, H-bridge circuits 230, 232 are shown in the configuration of FIG. 4 to allow further description of the use of the H-bridge circuits to provide active or passive recharge (i.e., recharge for removal of the DC polarization of the tissue electrode interface following a therapy pacing pulse being applied to a patient 14). For example, a passive recharge may be provided using H-bridge circuit 232 (wherein no capacitor is connected in series with the patient 14) when a patient is connected to the H-bridge circuit 232 as illustrated in the timing diagram of FIG. 6 ("Passive" timing line). For example, as shown in the Passive timing line of FIG. 6, an initial energy pulse 278 (e.g., a 1 millisecond pacing pulse, shown in FIG. 6) of a positive polarity may be applied by applying an input waveform to the input circuitry 142 representative thereof and by selection of current switching elements S1 and S4 (e.g., turning such switching elements on). A DC polarization may build up at the electrode/tissue interface during the initial energy pulse 278. By selection of current switching elements S2 and S4 during a period of time subsequent to the initial energy pulse 278, the DC polarization is removed over time (e.g., represented by the 20 millisecond reverse polarity waveform 279; shown in FIG. 6—Passive). All the waveforms shown in FIG. 6, for simplicity, are representative of voltage seen by the patient 14 connected to the H-bridge 232. As will be recognized, the current sensed by the circuit may be the same or different, depending on the type of recharge being performed.

Further, for example, the time to perform a passive recharge may be shortened (e.g., relative to a passive recharge without a series capacitor) by the using H-bridge circuit 230 having a capacitor 207 connected in series with the patient 14 when a patient 14 is connected to the H-bridge circuit 230 as illustrated by FIG. 4 and the timing diagram of FIG. 6 ("Passive (Cap)" timing line). For example, as shown in the Passive (Cap) timing line of FIG. 6, an initial energy pulse 280 (e.g., a 1 millisecond pacing pulse) of a positive polarity may be applied by applying an input waveform to the input circuitry 142 representative thereof and by selection of current switching elements S1 and S4 (e.g., turning such switching elements on). Energy is stored in capacitor 207 during the initial energy pulse 280. By selection of current switching elements S2 and S4 during a period of time subsequent to the initial energy pulse 280, the capacitor is allowed to drain through the patient 14 (e.g., represented by the less than 20 millisecond reverse polarity waveform 281; the current sense circuit would not see the discharge through the capacitor) removing the DC polarization of the tissue electrode interface and charge stored on capacitor 207 following the initial energy pulse 280 being applied to a patient 14.

In the passive recharge using capacitor 207 or not using the capacitor, either a static signal or a varying waveform (any arbitrary waveform) may be applied to the input circuitry 140 to control the initial energy pulse 280. Only three current switching elements (e.g., S1, S2, and S4; S1, S2 and S3; etc.) are required when passive recharging is performed. In other words, in one or more embodiments, one of the switches, for example, one of the high side current switching elements S1 or S3 may be eliminated or one of the low side switches S2, S4 may be eliminated. However, having all four current switching elements S1-S4 available allow for one or more functions of the circuitry to be performed, such as, programmable reversal of the energy pulses used to pace. For example, the initial energy pulse may be a negative polarity pulse by selection of current switching elements S2 and S3 (e.g., resulting in energy being stored in capacitor 207) and thereafter, turning current switching elements S3 and S4 on to drain the capacitor 207 during a subsequent time period.

In one or more embodiments, a further decrease in the amount of time required to remove the DC polarization of the tissue electrode interface (e.g., relative to the time required to perform a passive recharge) can be accomplished by applying an active recharge pulse such as with use of H-bridge circuit 232 (e.g., where there is no capacitor connected in series with the patient 14) or with use of H-bridge circuit 230 (e.g., where capacitor 207 is connected in series with the patient 14). For example, as shown in the "Active" timing line of FIG. 6, the waveform can be shaped to achieve a desired active recharge when capacitor 207 is not present, such as in H-bridge circuit 232. As shown in the "Active" timing line, with application of an input waveform to the input circuitry 140 representative thereof, the pulse waveform 285 shown in the "Active" timing line of FIG. 6 is seen by the patient upon selection of current switching elements S1 and S4 of H-bridge circuit 232 (e.g., turning such switching elements on). Thereafter, the active recharge portion 284 is applied (e.g., a 4 millisecond or less recharge waveform) by selection of current switching elements S2 and S3 of H-bridge circuit 232 during at least the application of an input waveform to the input circuitry 140 representative thereof removing the DC polarization at the tissue/electrode interface.

Still further, for example, as shown in the "Active (Cap)" timing line of FIG. 6, an active recharge through a series capacitor 207 using the H-bridge circuitry 230 may be performed. For example, an initial energy pulse 283 (e.g., a 1 millisecond pacing pulse) of a positive plurality may be applied by applying an input waveform to the input circuitry 140 representative thereof and by selection of current switching elements S1 and S4 of H-bridge circuit 230 (e.g., turning such switching elements on). The capacitor 207 stores charge thereon as a result of the initial pacing pulse 283. Thereafter, an active recharge portion of the input waveform may be applied to the input circuitry 140 (e.g., a 10 millisecond or less recharge waveform of a desired shape to achieve the desired recharge waveform) By selection of current switching elements S2 and S3 of H-bridge circuit 230 during at least the application of the active recharge pulse, an active recharge through the capacitor 207 is accomplished in a lesser time than required to perform a passive recharge (e.g., as represented by the 10 millisecond reverse polarity waveform 287 in the "Active (Cap)" timing line of FIG. 6 being less than the 20 millisecond waveform 279) removing the DC polarization of the tissue/electrode interface and energy stored on capacitor 207 following the initial energy pulse 283 being applied to a patient 14.

In the active recharge, for example, any suitable varying waveform may be applied to the input circuitry 140 to provide the initial energy pulse 285, 283 and recharge waveform 284, 287 suitable to remove the polarization. Using an active recharge allows for the sensing of an evoked response following recharge with less potential for false sensing due to the recharge being over earlier in the pacing cycle. Such evoked response sensing may be used by the control circuitry 202 to modify the arbitrary input signal 212 applied to input circuitry 210.

With further reference to FIG. 4, the constant current pacing apparatus 200 includes the constant current source 220 connected to the high side 234 of the H-bridge circuits 230, 232. In FIG. 4, the constant current source 220 includes a voltage source 221 and a voltage controlled current output circuit in the form of a FET 222 connected between the voltage source 221 and the high side 234 of the H-bridge circuits 230, 232. A diode 224 (e.g., a high voltage diode) is connected between the source of the FET 222 and the high side 234. In one or more embodiments, the FET 222 is operable in a linear mode (e.g., not in saturation) such that, when the constant current pacing apparatus 200 is operational, application of a gate to source voltage above the threshold voltage results in a constant source current output based on the gate to source voltage applied thereto. As shown in FIG. 4, the field effect transistor includes an n-channel MOSFET enhancement mode device. As such, upon application of $V_{GS}$ exceeding the $V_{TH}$ of the device, a generally proportional relationship exists between $V_{GS}$ and $I_D$ which is equivalent to $I_S$ and allows the constant current output of the constant current source 220 to follow the applied $V_{GS}$. For example, in one or more embodiments, such as when a capacitor 207 is not in the H-bridge circuit), a static $V_{GS}$ applied results in a static constant current output while a varied $V_{GS}$ applied results in a constant current output that follows the variation of $V_{GS}$ (e.g., the FET operates somewhat like a variable resistor in the linear mode).

The input circuitry 210 of the constant current pacing apparatus 200 drives the constant current source 220 connected to the high side 234 of the H-bridge circuits 230, 232, or in other words, in one exemplary embodiment, applies a $V_{GS}$ to n-channel enhancement-mode MOSFET device 222 that results in a constant source current output to the H-bridge circuits 230, 232. In the exemplary embodiment shown in FIG. 4, the input circuitry 210 includes operational amplifier 213 (e.g., high voltage operational amplifier). Operational amplifier 213 is configured as a comparator and is operating in open loop gain mode. The output of an operational amplifier, configured as a comparator, will vary its output at its maximum bandwidth to try and make the inputs match.

The feedback circuitry 240 along with the input circuitry 210 provide a feedback controlled loop for use in controlling application of the control voltage (e.g., $V_{GS}$) to the FET 222. An arbitrary input waveform 212 (e.g., a waveform between 0 to 2.5 volts) representative of the pacing stimulus to be delivered to a patient is applied to the non-inverting input thereof and a feedback input signal from feedback circuitry 240 representative of a pacing stimulus previously applied to a patient 14 is applied to the inverting input of the operational amplifier 213. The voltage output of the operational amplifier 213 is applied to FET 222 via resistor 214. A low pass filter 215 may be provided at the output of the operational amplifier 213 by connecting capacitor 216. This additional filter may be implemented as the dominant pole of the control loop to enhance repeatability in performance by removing variation in manufacturing bandwidth of the operational amplifiers in the circuit.

Feedback circuitry 240, as shown in the exemplary embodiment of FIG. 4, includes current sense circuit for sensing current flow through resistor 242 (e.g., equivalent to current delivered to the patient 14). The operational amplifier 244 is configured with a resistive feedback network 243 to amplify the voltage across resistor 242 that is directly representative of the current flowing through the H-bridge during the first phase of a pacing pulse or during active recharge. The voltage feedback output voltage of the operational amplifier configuration 244 for application to the inverting input of operational amplifier 213 of input circuitry 210 (e.g., the feedback circuit 240 operates as a current to voltage converting feedback circuitry to sense the current applied to the patient and provide a scaled up voltage feedback input signal to the input circuitry 210).

The configuration of the current sense circuit of feedback network 240, the configuration of the operational amplifier 213, and the low pass filter 215 may provide the dominant pole for the feedback controlled loop. The dominate pole of the feedback controlled loop is selected, in at least one embodiment, to provide a minimized oscillation of the constant current output when a substantial change in the input waveform 212 occurs (e.g., a step voltage change, a drop in voltage during application of an arbitrary waveform, etc.). For example, in one or more embodiments, by setting the corner frequency of filter 215 below the bandwidth of operational amplifier 213 it will slow down the slew rate (dV/dT) of the control voltage applied to the gate of 222. This in turn reduces the dI/dT of the current output though 222, thereby affording more opportunity for a lower speed (bandwidth) implementation of feedback network 240 to pass the feedback signal back to 213 (e.g., lower speed (bandwidth) operational amplifiers use less current, such as for battery powered configurations).

Further, for example, the constant current pacing apparatus 200 may include voltage sense circuitry 280 to sense voltage across a connected patient 14. The voltage sense circuitry 280 includes an operational amplifier 281 connected using a voltage divider network 282 to sense the voltage at the high side of the H-bridge circuits 230, 232 and provide a scaled voltage output to be sampled by control circuitry 202. Further, the current sense circuitry of feedback circuitry 240 also provides a sensed current signal 247 representative of the current flow applied to a connected patient 14. In other words, the control circuitry 202 samples both the voltage sense signal representative of voltage across a connected patient 14 and the current sense signal representative of current flow applied to a connected patient 14. The control circuitry 202 (e.g., processing circuitry) may then determine lead impedance from the sampled voltage sense signal and current sense signal (e.g., sensed voltage/sensed current). Such lead impedance, for example, may be used to determine if a lead has been dislodged or damaged (e.g., determine if a short or open is present in the circuit). For example, the control circuitry 202 may compare the lead impedance to acceptable range settings for such impedance to determine lead dislodgement or failure.

As described herein, a medical device such as an EPG 50 configured using the constant current pacing apparatus described herein, and an external defibrillator 42 (see FIG. 1) may not operate in a coordinated fashion and, thus, the EPG 50 may be exposed to high externally applied stimulation when the external defibrillator 42 is being used to deliver therapy to the patient 14. The source to drain diodes (e.g., body diode 274) connected across the source and drain of the field effect transistors of each of the current switching elements S1-S4 of the H-bridge circuits 230, 232 and the diode 224 connected between the FET 222 and high side 234 of the H-bridge circuits 230, 232 protect the EPG 50 from such high voltages applied, for example, from the external defibrillator device 42. One will recognize that any current switching elements may be used and associated with any suitable blocking circuitry (e.g., an IGBT with diode across the emitter/collector, a diode connected across the source/drain of a FET, etc.)

For example, upon application of such external high voltage across the patient 14, the diode 224 prevents external current flow from the H-bridge circuits 230, 232 to the constant current source 220. Further, the source to drain diodes connected across the field effect transistors of the current switching elements S1-S4 prevent undesirable current flow as well. For example, when a high voltage (positive) is applied at node 264, diode 224 is configured to block flow to FET 222 while the source to drain diode of S3 further blocks flow through the second leg 262 of the H-bridge circuit 232. Still further, the source to drain diode of S2 blocks flow through the first leg 261 of the H-bridge circuit 232 to ground. Still further, for example, when a high voltage (positive) is applied at node 265, diode 224 blocks flow to FET 222 while the source to drain diode of S1 further blocks flow through the first leg 261 of the H-bridge circuit 232. Still further, the source to drain diode of S4 blocks flow through the second leg 262 of the H-bridge circuit 232 to S2.

Figure 5:
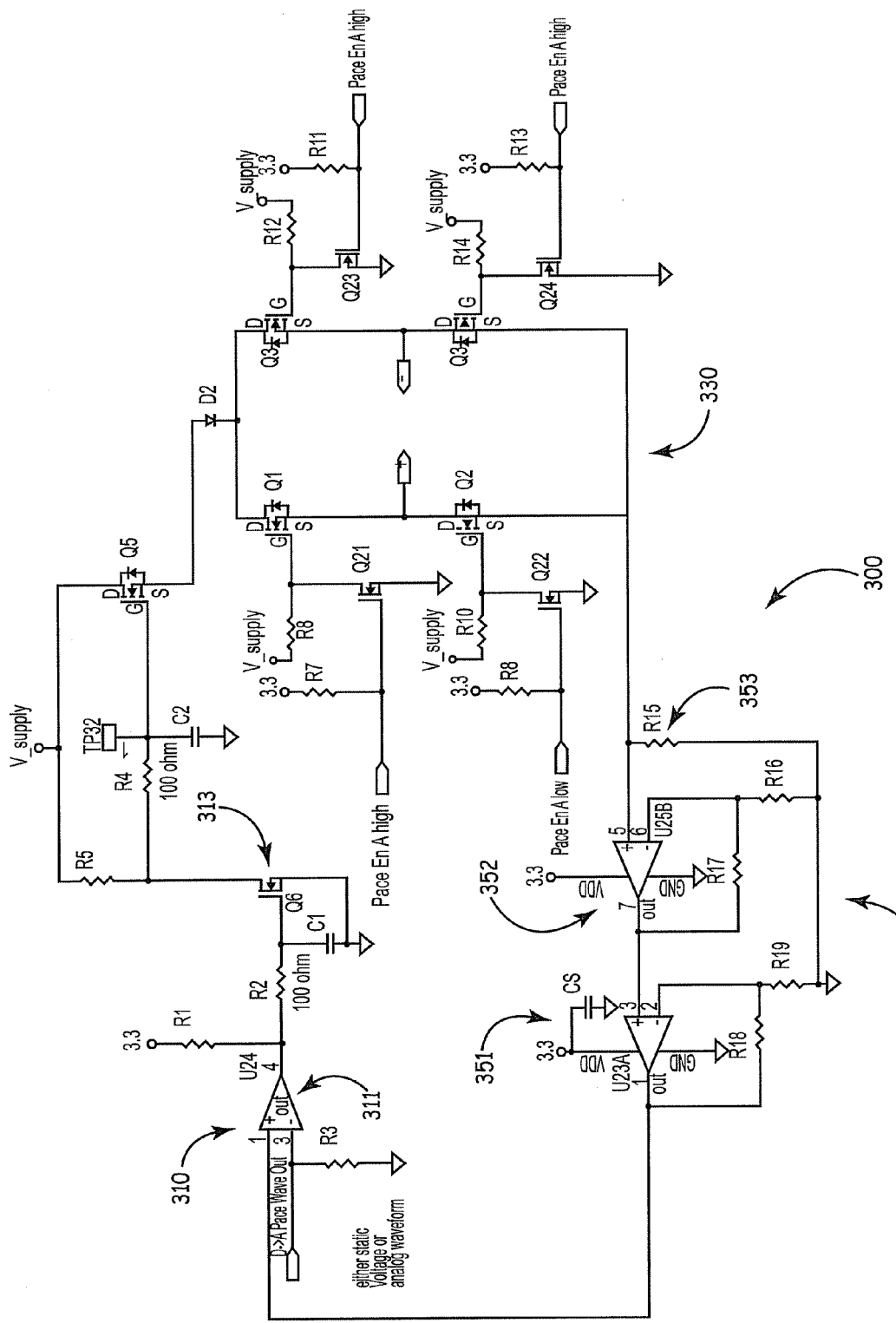
FIG. 5 shows an exemplary schematic diagram of another constant current pacing apparatus, such as functionally shown in FIG. 2.

FIG. 5 shows an exemplary schematic diagram of another constant current pacing apparatus 300, such as functionally shown in FIG. 2, to illustrate that various configurations of the constant current pacing apparatus are possible and that the description herein is not only limited to those described but that many equivalent circuits may be possible. FIG. 5 is substantially similar to FIG. 4 except that only a single H-bridge circuit 330 is used. Further, the input circuitry 310 is implemented using a low voltage operational amplifier 311 that provides an output for driving FET 313. The addition of a low gate threshold FET 313 allows operational amplifier 311 to be lower voltage, and as such, to be lower power than operational amplifier 213 shown in FIG. 4. FET 313 operates as a voltage level shifter to compensate for a significantly lower output voltage of operational amplifier 311.

Still further, feedback circuitry 350 is configured using two operational amplifiers 351, 352 as opposed as a single operational amplifier 244 as in FIG. 4. The operational amplifiers 351, 352 are configured as a multiple stage feedback circuit for sensing current through the current sense resistor 353 and providing a scaled up output voltage representative thereof for application to input circuitry 310. The addition of multiple gain stages allows for lower bandwidth, and subsequently lower power, operational amplifiers to be used, thereby reducing the total power consumption of the circuit.

All patents, patent documents, and references cited herein are incorporated in their entirety as if each were incorporated separately. This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

The invention claimed is:

1. A constant current pacing apparatus comprising:
an H-bridge circuit comprising a high side and a low side, wherein the H-bridge circuit comprises first and second legs connected between the high side and low side thereof, wherein the first leg of the H-bridge circuit comprises first and second current switching elements and the second leg of the H-bridge circuit comprises at least a third current switching element, wherein a patient is connectable to the first leg of the H-bridge circuit between the first and second current switching elements and to the second leg of the H-bridge circuit, wherein one of the first and second current switching elements along with the third current switching element define a pair of current switching elements such that, when the constant current pacing apparatus is operational and the pair of current switching elements are selected, a pacing stimulus having a first polarity is applied to the patient, and further wherein each current switching element of the H-bridge circuit is associated with a current blocking diode connected relative thereto; and
a constant current source connected to the high side or the low side of the H-bridge circuit, wherein, the constant current source, when the constant current pacing apparatus is operational, applies a constant current output to the H-bridge circuit, wherein a diode is connected between the constant current source and the H-bridge circuit to prevent external current flow from the H-bridge circuit to the constant current source, wherein the current blocking diodes associated with the current switching elements of the H-bridge circuit and the diode connected between the constant current source and the H-bridge circuit protect the constant current pacing apparatus from high voltage pulses applied to the patient via one or more other medical devices.

2. The apparatus of claim 1, wherein the first leg of the H-bridge circuit comprises the first and second current switching elements and the second leg of the H-bridge circuit comprises third and fourth current switching elements, wherein a patient is connectable to the first leg of the H-bridge circuit between the first and second current switching elements and the second leg of the H-bridge circuit between the third and fourth current switching elements, wherein one of the first and second current switching elements along with one of the third and fourth current switching elements define a first pair of current switching elements such that when the constant current pacing apparatus is operational and the first pair of current switching elements are selected a pacing stimulus having a first polarity is applied to the patient, and further wherein the other current switching elements define a second pair of current switching elements such that when the constant current pacing apparatus is operational and the second pair of current switching elements are selected a stimulus having a second polarity is applied to the patient, and further wherein current blocking diodes are associated with each of the first and second current switching elements and each of the third and fourth current switching elements for use in protecting the constant current pacing apparatus from high voltage pulses applied to the patient via one or more other medical devices.

3. The apparatus of claim 1, wherein the constant current pacing apparatus forms part of an external pulse generator.

4. The apparatus of claim 1, wherein each of the current switching elements comprises a field effect transistor and is associated with a current blocking body diode.

5. The apparatus of claim 1, wherein each of the current switching elements comprises identical components to the other current switching elements.

6. A method of providing constant current pacing to a patient, wherein the method comprises:
providing an H-bridge circuit comprising a high side and a low side, wherein the H-bridge circuit comprises first and second legs connected between the high side and low side thereof, wherein the first leg of the H-bridge circuit comprises first and second current switching elements and the second leg of the H-bridge circuit comprises at least a third current switching element, wherein a patient is connectable to the first leg of the H-bridge circuit between the first and second current switching elements and to the second leg of the H-bridge circuit, wherein one of the first and second current switching elements along with the third current switching element define a pair of current switching elements such that, when the constant current pacing apparatus is operational and the pair of current switching elements are selected, a pacing stimulus having a first polarity is applied to the patient, and further wherein each current switching element of the H-bridge circuit is associated with a current blocking diode connected relative thereto;
providing a constant current source connected to the high side or the low side of the H-bridge circuit, wherein a diode is connected between the constant current source and the H-bridge circuit;
controlling the constant current source to generate a constant current output to be applied to the H-bridge circuit for application of a pacing stimulus to the patient upon selection of the pair of current switching elements; and using the current blocking diodes associated with each current switching element of the H-bridge circuit and the diode connected between the constant current source and the H-bridge circuit to provide protection from high voltage pulses applied to the patient via one or more other medical devices.

7. The method of claim 6, wherein the first leg of the H-bridge circuit comprises the first and second current switching elements and the second leg of the H-bridge circuit comprises third and fourth current switching elements, wherein a patient is connectable to the first leg of the H-bridge circuit between the first and second current switching elements and the second leg of the H-bridge circuit between the third and fourth current switching elements, wherein one of the first and second current switching elements along with one of the third and fourth current switching elements define a first pair of current switching elements such that when the constant current pacing apparatus is operational and the first pair of current switching elements are selected a pacing stimulus having a first polarity is applied to the patient, and further wherein the other current switching elements define a second pair of current switching elements such that when the constant current pacing apparatus is operational and the second pair of current switching elements are selected a stimulus having a second polarity is applied to the patient, wherein current blocking diodes are associated with each of the first and second current switching elements and each of the third and fourth current switching elements, and further wherein the method comprises using the current blocking diodes associated with each of the first and second current switching elements and each of the third and fourth current switching elements of the H-bridge circuit and the diode connected between the constant current source and the H-bridge circuit to provide protection from high voltage pulses applied to the patient via one or more other medical devices.

8. The method of claim 6, wherein the constant current pacing is applied to a patient using an external pulse generator that comprises the H-bridge circuit and constant current source.

9. The method of claim 6, wherein each of the current switching elements comprises a field effect transistor and is associated with a current blocking body diode.

10. The method of claim 6, wherein each of the current switching elements comprises identical components to the other current switching elements.

* * * * *